United States Patent [19]
Fixel et al.

[11] 3,990,116
[45] Nov. 9, 1976

[54] PRETENSIONED PROSTHETIC DEVICE FOR SKELETAL JOINTS

[76] Inventors: Irving E. Fixel, 3705 Hollywood Blvd., Hollywood, Fla. 33022; J. Lawrence Katz, 838 Maxwell Drive, Schenectady, N.Y. 12309

[22] Filed: Oct. 17, 1974

[21] Appl. No.: 515,485

[52] U.S. Cl. .................................. 3/1.91; 3/1.911; 128/92 C
[51] Int. Cl.² ........................................ A61F 1/24
[58] Field of Search .......................... 3/1, 1.9–1.913, 3/22, 29; 128/92 C, 92 CA

[56] References Cited
UNITED STATES PATENTS

| 3,426,364 | 2/1969 | Lumb | 3/1.91 |
|---|---|---|---|
| 3,739,403 | 6/1973 | Nicolle | 3/1.91 |
| 3,765,033 | 10/1973 | Goldberg et al. | 3/1.911 |
| 3,848,276 | 11/1974 | Martinez | 3/1.911 |

FOREIGN PATENTS OR APPLICATIONS

| 497,998 | 5/1930 | Germany | 3/29 |
|---|---|---|---|
| 1,902,700 | 8/1970 | Germany | 3/1.91 |

*Primary Examiner*—Ronald L. Frinks

[57] ABSTRACT

An improved pretensioned prosthetic device is disclosed which incorporates pretensioned or biased spring means to provide a skeletal joint such as a finger or knee joint with a controlled flex and reflex action.

8 Claims, 5 Drawing Figures

U.S. Patent      Nov. 9, 1976      3,990,116
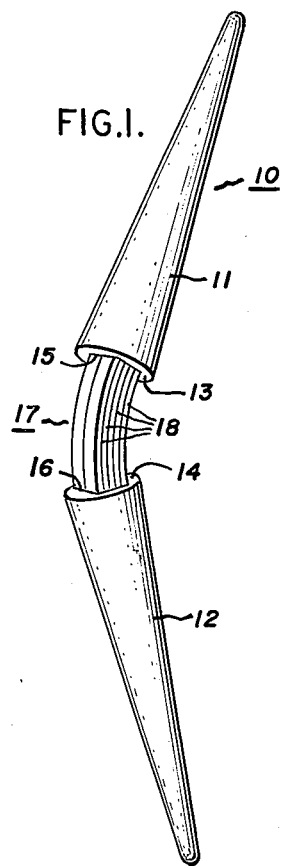
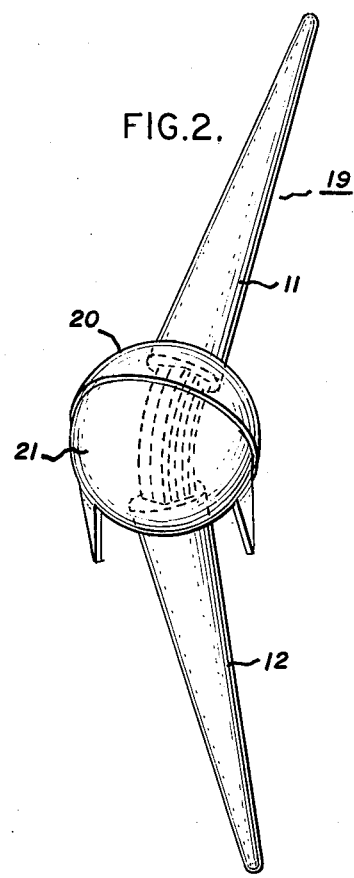
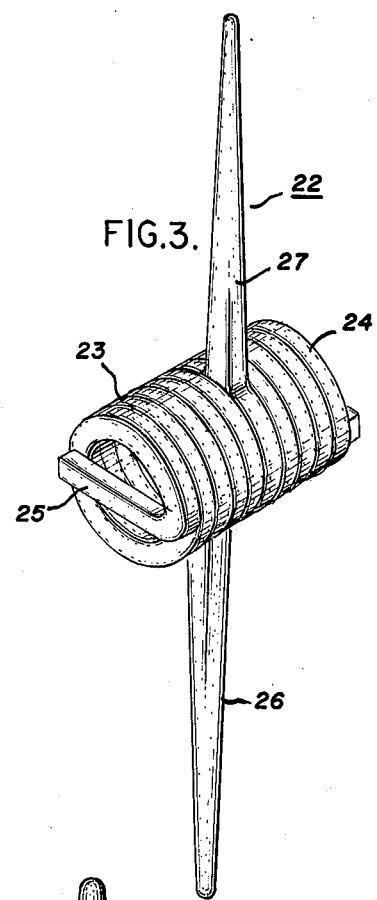
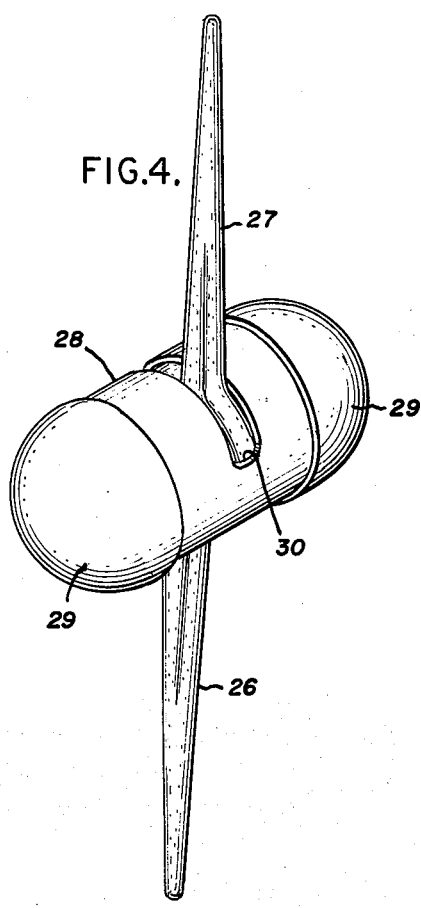
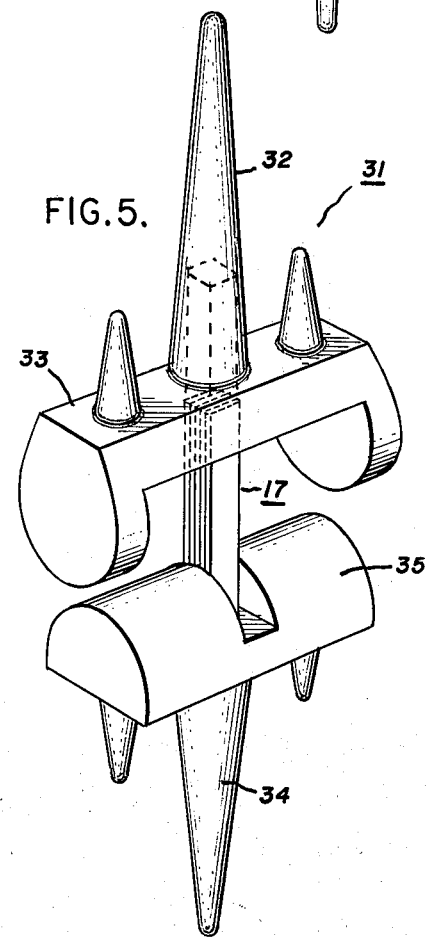

PRETENSIONED PROSTHETIC DEVICE FOR SKELETAL JOINTS

BACKGROUND OF THE INVENTION

1. Field of the Invention

This invention relates to a skeletal joint prosthetic device and more particularly to knee and finger joints which have pretensioned or biasing spring means which provide them with predetermined and inherent controlled flexion.

2. Description of the Prior Art

In previous prosthetic devices the mechanical elements or components were designed primarily to provide the required free motion and were not designed to include any significant controlling or restraining of the intermediary phases of motion, once motion is started. For example, in a replacement knee joint, the joint is usually designed so that it is freely pivotal, within limits, and motion is provided solely by the muscular ability and coordination of the patient. The joint itself does not have inherent forces therein which aid or complement the existing available muscular ability and coordination of the patient.

Prior replacement finger joints are usually provided with a proper or natural curvature so that the hand may be employed to grasp some object when the object is inserted into the closed configuration of the hand. However, no muscular proportioning is accomplished between the natural resiliency of the finger prosthesis which is usually a silicone rubber or similar material implant, and the remaining muscle ability of the hand.

It has been discovered that an improved prosthetic joint may be provided by incoroporating a significantly pretensioned biasing means in the device the action of which can be correlated to the muscular ability of the patient.

OBJECTS OF THE INVENTION

Accordingly, it is an object of this invention to provide an improved pretensioned prosthetic joint.

It is a further object of this invention to provide an improved prosthetic joint which is pretensioned in predetermined directions.

It is another object of this invention to provide a prosthetic joint which is pretensioned by internal spring biasing means.

It is a further object of this invention to provide a prosthetic joint having a decreasing deflection vs. load ratio.

It is yet another object of this invention to provide a calibrated spring assembly means in a pretensioned prosthetic joint.

SUMMARY OF THE INVENTION

In one preferred form, this invention involves a prosthetic joint which is pretensioned or preflexed, for example, by spring means incorporated internally in the joint which is to provide a biasing force in a predetermined direction. The biasing force is correlated to the available muscular ability so that motion of the joint is expedited or a predetermined position of the joint is favored.

BRIEF DESCRIPTION OF THE DRAWINGS

This invention will be better understood when taken in connection with the following description and drawings in which FIG. 1 is an illustration of a leaf spring pretensioned prosthetic device particularly adaptable for limited motion of joints, such as finger joints and knee joints.

FIG. 2 is an illustration of a modification of the pretensioned leaf spring prosthetic device of FIG. 1.

FIG. 3 is an illustration of a pretensioned coil spring prosthetic device.

FIG. 4 illustrates the FIG. 3 device within a suitable housing.

FIG. 5 is an illustration of a limited motion bearing joint having a leaf spring assembly incorporated therewith.

DESCRIPTION OF PREFERRED EMBODIMENTS

Referring now to FIG. 1, there is disclosed a finger joint prosthesis although the structure is adaptable as well for other joints. In FIG. 1 the pretensioned spring joint 10 comprises opposed support members 11 and 12 which may be bone receptive members, i.e. the peg or spike members which are specifically adapted to be inserted into the bone structure at opposite sides of a given joint. These members may be made of various metals or non-metals or combinations thereof. The metals may include those which are relatively inert or non-reactive to body tissues such as stainless steel and vitallium. One of the support members 11 or 12 may be of metal while the other may be of a polymeric material such as silicone rubber or polyethylene. The opposed ends 13 and 14 of the support members have suitable axial apertures or cavities 15 and 16 to receive and retain therein in any suitable manner a pretensioned spring assembly 17.

Spring assembly 17 may comprise many well known forms of biasing springs such as leaf springs, coil springs, volute springs, etc. In a preferred form of this invention pretensioned spring assembly 17 comprises a plurality of individual leaf springs 18 which provide a predetermined tensioned deflection for joint 10. The individual springs 18 may be small metal rods, bars or thin sections of similar cross section, and may also comprise a selection of springs of different metals, and combinations of metals and non-metals as well as combinations of springs of different cross-sectional configurations. The leaf spring assembly 17, if for a finger joint, is usually made up so that the support members 11 and 12 are angularly disposed relative to each other and the normal opening of the hand or fingers by the patient with their related muscles is the force tending to place supports 11 and 12 in coaxial or opposing relationship. The individual spring members 18 are selected so that rapidly increasing forces are required to progressively open the fingers, and the required force is correlated to the available muscular control and condition of the patient.

This kind of correlation may permit the patient to use mostly his own muscular development to pick up or grasp objects lightly, and at the same time provide increasing spring return action for heavier objects. These features are based upon the joint being pretensioned, i.e. being biased in one direction.

Pretensioned as used in this specification includes one or more of the following spring characteristics:

a. where the spring in its operative environment is under a tension or deflecting force, for example, a bent or curved spring which requires a greater deflecting force to straighten it than to increase its curvature;

b. where the spring has a deflection versus load ratio which diminishes with increasing loads, for example, as occurs in leaf springs or other springs where cross-section varies decreasingly with length.

In a finger joint the joint action can be best described as relating somewhat to the cantilever beam deflection principle. If a cantilever beam were of a relatively constant cross-section and were of a silicone rubber material, for example, increasing load increments at the end of the beam would cause deflections which would greatly increase per increment of loading. A skeletal joint such as a finger joint may be replaced with a solid but flexible beam bridging the joint. However, with the prior rubbery materials (or the metal hinge implant with its free motion) the bias or closing force of a finger or fingers at their maximum semi-opening or grasping position is less than desirable. Since the total thickness of the joint is also limited, merely thickening of the beam to a maximum may not provide the desirable increase in a biasing or closing force. Furthermore, thick materials or moderately thick materials of high density do not lend themselves to maximum deflections desirable in finger joints. However, with a slender metal beam the flexibility, and prebiasing or pretensioning, may be predetermined by the cross-sectional thickness of the beam material, taken in connection with the muscular ability of the patient. In the present invention the spring assembly 17 may be considered as the beam whose axial length is now confined to the short distance between support members 11 and 12. The spring assembly 17 of this invention may be designed to easily correlate the travel distance of an opening hand or finger with the increasing returning force of elasticity in the spring over a wide range of action. It provides a beam configuration which allows initially greater travel or deflection in the early stages with a sharper degree of closing forces in the later stages. In order to provide this action a multiple leaf spring configuration 18 of FIG. 1 is employed. The advantage of a leaf type spring is that a closer correlation can be produced in a smaller volume for the desired deflection versus tension ratio. At the same time there is no single point of stress or fatigue in the individual leaves and the tension forces are distributed and diffused throughout the total system.

The leaf spring assembly 17 of FIG. 1 may be retained in support members 11 and 12 so that there is relative motion between springs 18 during flexing of the joint. For example, they may simply be free floating in the apertures or cavities 15 and 16, or mechanically retained therein. The affixation means or free floating means should take into consideration that the spring assembly 17 also provides for some torsional deflection. Certain plastic materials such as nylon, silicone rubber and polyethylene may be interleaved with springs 18 to provide lubrication and ease of flexing.

In some instances it may be desirable to enclose the spring assembly 17 of FIG. 1, or to provide a natural bone joint configuration, or to shield or isolate the spring members 18, as illustrated in FIG. 2. In FIG. 2 the spring joint 19 comprises a pair of interfitting hollow hemispherical members 20 and 21 which provide an enclosure throughout the design range of movement of support members 11 and 12.

The spring joint of this invention may also utilize other spring forms. For example, the spring joint 22 of FIG. 3 comprises a coil spring which is dimensioned to provide the kind of action evidenced by the leaf spring assembly 17 of FIG. 1. In FIG. 3, the spring joint 22 comprises a pair of coil tension springs 23 and 24 of preferably rectangular cross section. Each spring is wound so that one end, for example, end 25 of spring 23, becomes a spring lock and the other end becomes a stem 26. Spring 24 is wound in the same manner so that its stem 27 is coaxially and oppositely disposed with respect to stem 26.

To provide the requisite stability for the spring joint 22, the springs 23 and 24 are suitably contained in a cylindrical housing 28 of an appropriate metal such as vitallium. Such a housing 28 is illustrated in FIG. 4 complete with end caps 29 and slots 30 to provide deflection of the stems 26 and 27. For lubrication purposes a thin sleeve of silicone rubber or polyethylene material may be placed within housing 28 and between it and the springs 23 and 24. The springs 23 and 24 may be of constant or varying cross section although the relatively large torsion coil design is effective in the first instance to provide the desirable flexion tension ratio over a wide range of motion.

The spring joints of FIGS. 1 and 3 may comprise the entire joint assembly or for the purposes of stability and load carrying ability these spring joints may be combined with sliding action joints such as a ball and socket or wrist pin joint, particularly for hip joint use. Referring now to FIG. 5, a spring joint 31 comprises an upper support member 32 and a generally cylindrical bearing housing or journal 33. A lower support member 34 carries with it a bearing member 35. A spring assembly such as that shown in FIG. 1 as assembly 17, is positioned in spring joint 31 so that one end of the spring assembly 17 passes into and is retained by upper support member 32. The other end of spring assembly 17 fits into and is retained in lower support member 34. Leaf spring assembly 17 is pretensioned or biased so that it complements the patient's muscular system. Spring assembly 17 may be designed or carefully calibrated to react in a predetermined manner and to take up a predetermined central position as shown, or an off center position.

The spring joint 31 of FIG. 4 may be manufactured from various metals such as medically approved stainless steel, vitallium and other metals which are significantly inert with respect to bodily tissues. The lower support member 34, the tibial part, may also have its section 35 made of polyethylene or any other bio-compatible polymer, for natural lubrication purposes, or the entire lower support member may be made of polyethylene or other material which will provide good lubricating characteristics with upper member 33. Spring joint 31 of FIG. 4 may also include a plurality of spring assemblies spaced along the bearing support or a system of spring assemblies may be employed wherein one or more of the assemblies are in tandem.

This invention thus provides a prosthetic device which has incorporated therewith a calibrated pretensioned spring assembly which in turn is correlated to the muscular ability of the patient to assist the muscular ability during joint motion. Such a joint may provide a greater force or biasing action in one direction where that particular muscular action is weakened. The joint may also have a biased centroidal position so that the joint has a natural tendency to return to a balanced position, an important factor in hip and knee joints.

While other modifications of this invention and variations of apparatus may be employed within the scope of this invention and have not been described or illustrated, the invention is intended to include all such modifications as may ordinarily be embraced within the following claims.

What I claim as new:

1. A prosthetic device for skeletal joints comprising in combination
   a. a single pair of columnar support members,
   b. each said support members having one end thereof adapted for attachment to spaced skeletal bones with their other ends in opposed adjacent relationship,
   c. and a separate spring member comprising a multiple leaf spring connecting said support members to provide a flexible pivotal prosthetic joint for said bones,
   d. said spring member being pretensioned in a predetermined direction so that a greater bending force is required to flex the spring member in one direction as compared to the force required to flex the spring member in an opposite direction.

2. The invention of claim 1 wherein an enclosure surrounds said pretensioned spring member.

3. A prosthetic device comprising in combination
   a. a pair of columnar support members,
   b. each said support members having one end thereof adapted for attachment to respective spaced skeletal bones with their other ends in opposed adjacent relationship,
   c. bearing means rigidly affixed to each opposed adjacent end and interconnecting the other ends of said support members in bearing relationship to provide for angular motion of said bone members relative to each other,
   d. a pretensioned spring member within and extending from one of said support members and through said bearing means and into the other of said support members,
   e. said spring member being of a structural configuration to bias said support members in a predetermined position and to require a greater force to bend said spring member in one direction as compared to a force required to bend said spring member in an opposite direction.

4. The invention of claim 3 wherein said bearing is a ball and socket joint.

5. The invention of claim 3 wherein one of said members is a non-metal.

6. The invention of claim 3 wherein said spring is a leaf spring.

7. The invention of claim 6 wherein said leaf spring is a multiple leaf spring.

8. A prosthetic device for skeletal joints comprising in combination
   a. a single pair of columnar support members,
   b. each said support members having one end thereof adapted for attachment to spaced skeletal bones with their other ends in opposed adjacent relationship,
   c. each said other ends defining one end of a coil spring to provide a pair of adjacent coil springs in coaxial and opposite relationship whose axis is transverse to the axis of said support members,
   d. an enclosure surrounding said coil springs,
   e. each said coil springs being pretensioned in a predetermined direction so that a greater force is required to deflect its support member in one direction to rotate said spring on its axis as compared to the force required to deflect the support in an opposite direction.

* * * * *